United States Patent
He et al.

(10) Patent No.: US 11,744,490 B2
(45) Date of Patent: Sep. 5, 2023

(54) NON-INVASIVE BLOOD GLUCOSE DETECTION DEVICE AND MEASUREMENT METHOD BASED ON MULTI-TECHNOLOGY INTEGRATION

(71) Applicant: Shanghai Institute of Technical Physics, Chinese Academy of Sciences, Shanghai (CN)

(72) Inventors: Zhiping He, Shanghai (CN); Jinning Li, Shanghai (CN); Halting Zhao, Shanghai (CN); Qiujie Yang, Shanghai (CN); Feifei Li, Shanghai (CN)

(73) Assignee: Shanghai Institute of Technical Physics, Chinese Academy of Sciences, Shanghai (CN)

( * ) Notice: Subject to any disclaimer, the term of this patent is extended or adjusted under 35 U.S.C. 154(b) by 423 days.

(21) Appl. No.: 17/148,065

(22) Filed: Jan. 13, 2021

(65) Prior Publication Data
US 2021/0330217 A1    Oct. 28, 2021

(30) Foreign Application Priority Data
Apr. 23, 2020   (CN) ......................... 202010324644.1

(51) Int. Cl.
*A61B 5/1455*    (2006.01)
*A61B 5/145*     (2006.01)
*A61B 5/00*      (2006.01)

(52) U.S. Cl.
CPC ........ *A61B 5/1455* (2013.01); *A61B 5/14532* (2013.01); *A61B 5/742* (2013.01)

(58) Field of Classification Search
CPC .............. A61B 5/1455; A61B 5/14551; A61B 5/14552; A61B 5/14532; A61B 5/14558; A61B 5/742
See application file for complete search history.

(56) References Cited

U.S. PATENT DOCUMENTS

| 5,541,413 A * | 7/1996 | Pearson ................. G01N 21/94 250/341.8 |
| 9,662,004 B2 * | 5/2017 | Li ...................... A61B 5/14558 |
| 2003/0225321 A1 * | 12/2003 | Cote ..................... G01N 21/39 600/318 |
| 2017/0020385 A1 * | 1/2017 | Matsushita ........ A61B 5/14507 |

* cited by examiner

*Primary Examiner* — Chu Chuan Liu
(74) *Attorney, Agent, or Firm* — SAGE PATENT GROUP

(57) ABSTRACT

A non-invasive blood glucose detection device and a measurement method based on a multi-technology integration is provided according to the disclosure. The device combines a near-infrared spectroscopy non-invasive blood glucose detection technology with a non-invasive blood glucose detection technology based on optical polarimetry, thus improving the detection sensitivity and accuracy, simultaneously inhibiting the influence of human background and individual differences. The AOTF can be used to achieve tunable light splitting and the output lights have two orthogonal linearly polarized light characteristics. The hardware for implementing the two methods are combined. Thus, the device has the advantages of simple structure, strong anti-interference ability and low cost. In addition, it combines the two methods on software by adopting a random forest algorithm and a data fusion algorithm, which effectively improves the prediction accuracy of non-invasive blood glucose concentration.

5 Claims, 2 Drawing Sheets

NON-INVASIVE BLOOD GLUCOSE DETECTION DEVICE AND MEASUREMENT METHOD BASED ON MULTI-TECHNOLOGY INTEGRATION

CROSS REFERENCE TO RELATED APPLICATION

This application claims the priority of Chinese Patent Application No. 202010324644.1 entitled "Non-invasive Blood Glucose Detection Device and Measurement Method Based on Multi-technology Integration" filed with the Chinese Patent Office on Apr. 23, 2020, which is incorporated herein by reference in its entirety.

FIELD

The disclosure relates to the field of human blood glucose detection, in particular to a high-precision non-invasive blood glucose detection device and measurement method.

BACKGROUND

Regular and continuous blood glucose detection has important values for understanding blood glucose changes of diabetic patients, helping doctors to determine the optimal treatment scheme, accurately using medicines and delaying the development of diseases. The conventional blood glucose detection methods are mainly to extract a blood sample for analysis in a hospital or to test the blood glucose through test strips in a fingers prick manner. These methods all need to pierce the skin, and frequent blood collection not only makes the patient psychologically afraid, but also easily causes infection. In addition, the detection cost is high, and continuous blood glucose monitoring cannot be achieved.

At present, non-invasive blood glucose detection technology mainly includes optical method, a method of conservation of energy metabolism, human body fluid method and the like. Among the many research methods, the optical method has the characteristics of rapidness, non-invasive, multi-dimensional information and the like, which is the main research field of the non-invasive blood glucose detection at present. Common optical detection methods include Raman spectroscopy, photoacoustic spectroscopy, fluorescence, optical coherence imaging, optical polarimetry, and near-infrared spectroscopy, in which the research of the near-infrared spectroscopy and the optical polarimetry have attracted much attention from researchers. The near-infrared spectroscopy utilizes a characteristics of a good linear correlation between near-infrared light absorption and human blood glucose concentration, which has a series of advantages such as strong penetrability and high signal sensitivity and the like. Some published documents report the near-infrared spectroscopy. For example, the patent CN 103349553B discloses a dual-wavelength differential near-infrared non-invasive glucometer, which combines the amplitude and phase characteristics of near-infrared light, and utilizes a difference between the peak and trough of absorption spectrum to achieve high-precision non-invasive blood glucose detection. The patent CN108593593A discloses a non-invasive blood glucose measuring device which is used to detect and analyze blood glucose using serial dual infrared spectroscopy. In this method, a single light source and a single sensor are adopted to avoid the influence of errors caused by differences in light sources or sensors. The patent CN 110575181A discloses a method for training a network model of a near-infrared spectroscopy non-invasive blood glucose detection, which optimizes near-infrared detection accuracy in a neural network algorithm. However, the current near infrared spectroscopy non-invasive blood glucose measurement technology still faces problems such as individual difference in human and difficulty in deducting interference signal from human tissue, etc., which affect the accuracy and stability of the method.

A non-invasive blood glucose detection technology based on optical polarimetry is a method for detecting blood glucose by using principle of optical polarized light. It utilizes the unique optical polarimetry characteristic of glucose. Namely, when one beam of linearly polarized light passes through glucose solution, the transmission light is linearly polarized light, and there is an angle between the polarization directions of an incident light and the transmission light. The angle is related to the concentration of glucose. Since other components of human tissues have no optical polarimetry characteristics, this method is not affected by human background interference. At present, the non-invasive blood glucose detection technology based on optical polarimetry mostly uses orthogonal dual-polarized light detection technology to achieve blood glucose concentration detection. As described in the patent CN 100482162C, the measured blood glucose signal is converted into the signal intensity difference in two polarization directions by orthogonal dual-polarized light, and the blood glucose concentration is determined by the signal intensity difference. However, the method uses electro-optic crystal modulation to generate orthogonal dual-polarized light. Since the modulation voltage of plus or minus 180V is required, small changes in the voltage will seriously interfere with the weak blood glucose signal. Therefore, the method has poor anti-interference ability, and the device structure is complex, and it is difficult to achieve high-precision non-invasive blood glucose detection.

It can be seen that the near-infrared spectroscopy non-invasive blood glucose detection technology has the advantages of a high linearity between absorption intensity and blood glucose concentration, strong detection signal sensitivity, and simple device structure and the like. However, the interference of human background noise has a greater impact on the detection results. The non-invasive blood glucose detection method based on optical polarimetry does not have the influence of human background noise, but it has disadvantages such as complex detection equipment and poor anti-interference ability and the like. If the two technical methods can be combined through effective means, it can be realized that the near-infrared spectroscopy technology has the advantages of better linearity in spectral absorption and blood glucose concentration, and higher signal sensitivity, and meanwhile the human background noise can be inhibited, and the blood glucose detection precision can be improved.

SUMMARY

In view of the difficulty in achieving high-precision non-invasive blood glucose detection with an existing single technology, a non-invasive blood glucose detection device and measurement method based on a multi-technology integration is provided according to the disclosure, which is based on complementary characteristics of near-infrared spectroscopy non-invasive blood glucose detection technology and non-invasive blood glucose detection technology based on optical polarimetry. An acousto-optic tunable filter (AOTF) is used to realize tunable light splitting. That is, two emitted beams of positive and negative first-level monochromatic light are orthogonal linearly polarized light. In this way, the two methods is integrated to achieve the purpose of improving the accuracy of blood glucose detection.

The technical scheme of the disclosure is as follows.

A non-invasive blood glucose detection device based on a multi-technology integration includes a main controller module 1, a display module 2, an AOTF monochromatic light source module 3, a detection probe module 4 and a data processing module 5, as shown in FIG. 1. The main controller module 1 controls the AOTF monochromatic light source module 3 to generate near-infrared orthogonal polarization monochromatic light which is transmitted to the detection probe module 4 through an optical fiber. The detection probe module 4 emits the near-infrared orthogonal polarization monochromatic light to a detection part. The detection probe module 4 collects the near-infrared orthogonal polarization monochromatic light reflected by the detection part, and converts an optical signal into an electric signal with polarization information and absorption intensity information. The detection probe module 4 transmits the electric signal to the data processing module 5. The data processing module 5 processes the electric signal and performs an A/D conversion on the electric signal, and then transmits the converted signal to the main controller module 1. The main controller module 1 predicts a blood glucose value and displays the predicted blood glucose value on the display module 2.

The AOTF monochromatic light source module 3 includes a halogen lamp 3-1, a collimating lens 3-2, an AOTF 3-3, a focusing lens 3-4, an optical fiber combiner 3-5, a polarization maintaining fiber 3-6, a radio frequency power amplifier 3-7 and a radio frequency generator 3-8, as shown in FIG. 1. The main controller module 1 controls the radio frequency generator 3-8 to generate a signal with a specified frequency. The signal is amplified by the radio frequency power amplifier 3-7 and the amplified signal is output to the AOTF 3-3. The main controller module control the halogen lamp 3-1 to turn on and emits a polychromatic light beam. The polychromatic light beam is collimated by the collimating lens 3-2, and then is incident to the AOTF 3-3. The polychromatic light beam passes through the AOTF 3-3, to generate two beams of positive and negative first-level near-infrared monochromatic light with orthogonal polarization states. Two light beams are coupled into the polarization maintaining fiber 3-6 through the focusing fiber lens 3-4. The light beams pass through the optical fiber combiner 3-5, to generate a beam of near-infrared orthogonal polarization monochromatic light. The near-infrared orthogonal polarization monochromatic light is transmitted to the detection probe module 4 by the polarization maintaining fiber 3-6.

The detection probe module 4 includes a transmitting probe unit 4-1, a receiving probe unit 4-2, a Y-shaped polarization maintaining fiber 4-3, a near-infrared photoelectric detector 4-4, an analyzer 4-5 and a photoelectric receiver 4-6, as shown in FIG. 2. The AOTF monochromatic light source module 3 transmits the near-infrared orthogonal polarization monochromatic light to the transmitting probe unit 4-1 through the polarization maintaining fiber. The light beam reflected by the detection part is received by the receiving probe unit 4-2. The receiving probe unit 4-2 couples the received light beam to output into the Y-shaped polarization maintaining fiber 4-3. The light beam splits into two beams by the Y-shaped polarization maintaining fiber 4-3. One beam enters the near-infrared photoelectric detector 4-4 to generate a near-infrared intensity signal; and the other beam enters the analyzer 4-5, and then is received by the photoelectric receiver 4-6. The photoelectric receiver 4-6 generates a light intensity signal with deflection angle information. The near-infrared light intensity signal and the polarization angle signal are transmitted to the data processing module 4 for processing. The data processing module 4 amplifies and filters the near-infrared photoelectric intensity signal and the polarization angle signal, performs an analog-to-digital conversion on the processed near-infrared photoelectric intensity signal and the polarization angle signal, and transmits to the main controller module 1 the signal on which the analog-to-digital conversion is performed. The main controller module 1 analyzes the signal and predicts the blood glucose value.

The disclosure also provides a non-invasive blood glucose measurement method which is a combination of near-infrared spectroscopy non-invasive blood glucose detection technology and a non-invasive blood glucose detection technology based on optical polarimetry. The method includes the following steps:

Step 1: changing a wavelength of near-infrared orthogonal dual-polarization monochromatic light output by the AOTF monochromatic light source 3 with t as a step, collecting near-infrared intensity data and polarization angle data at m sampling points, and storing the data of the m sampling points into the main controller module 1, where t is the wavelength in unit of nm;

Step 2: predicting a final blood glucose value in a random forest algorithm and a data fusion algorithm by the main controller module, wherein in the step 2, the blood glucose concentration is predicted by following steps:

Step 2-1: performing digital filtering and correction on the stored m near-infrared light intensity data and m light beam polarization angle data by the main controller module 1;

Step 2-2: after the digital filtering and correction, obtaining a blood glucose value BG1 predicted by a near-infrared spectroscopy and a blood glucose value BG2 predicted by an optical polarimetry in a random forest algorithm respectively;

Step 2-3: performing, by the main controller module 1, correlation analysis on blood glucose values predicted by the two methods; distributing weights according to correlation analysis results; and performing data fusion according to a following formula to calculate a final blood glucose concentration:

$$BG=a*BG1+b*BG2+c$$

wherein a and b are weights obtained by the correlation analysis, c is a correction coefficient, and an obtained blood glucose value BG is controlled and displayed on the display module 2 through the main controller module 1.

The disclosure has the following beneficial effects. In the device according to the disclosure, a near-infrared spectroscopy non-invasive blood glucose detection technology is combined with a non-invasive blood glucose detection technology based on optical polarimetry, thus improving the detection sensitivity and accuracy and inhibiting the influence of human background and individual differences. The AOTF can be used to achieve tunable light splitting and the output lights have two orthogonal linearly polarized light characteristics. The hardware for implementing the two methods are combined. Thus, the device has the advantages of simple structure, strong anti-interference ability and low cost. In addition, it combines the two methods on software by adopting a random forest algorithm and a data fusion algorithm, which effectively improves the prediction accuracy of non-invasive blood glucose concentration. It can realize the purpose of high-precision non-invasive blood glucose concentration detection.

DETAILED DESCRIPTION

The disclosure will be further described in detail below with reference to the accompanying drawings.

Figure 1:
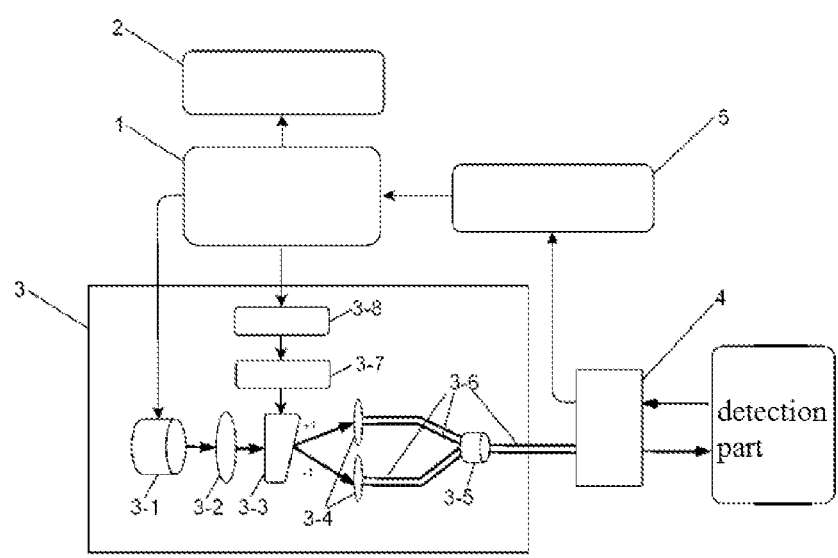
FIG. 1 is a structural diagram of a non-invasive blood glucose detection device based on a multi-technology integration.

As shown in FIG. 1, a non-invasive blood glucose detection device based on a multi-technology integration are provided according to an embodiment of the disclosure, which includes a main controller module 1, a display module 2, an AOTF monochromatic light source module 3, a detection probe module 4 and a data processing module 5. As shown in FIG. 1, the main controller module 1 controls the AOTF monochromatic light source module 3 to generate near-infrared orthogonal polarization monochromatic light which is transmitted to the detection probe module 4 through an optical fiber. The detection probe module 4 emits the near-infrared polarization monochromatic light to a detection part. The detection probe module 4 collects the near-infrared polarization monochromatic light reflected by the detection part and converts optical signal into electric signal with polarization information and absorption intensity information. The detection probe module 4 transmits the electric signal to the data processing module 5. The data processing module 5 processes the electric signal and performs an A/D conversion on the electric signal, and then transmits the converted signal to the main controller module 1. The main controller module 1 predicts the blood glucose value and displays the predicted blood glucose value on the display module 2.

The AOTF monochromatic light source module 3 includes a halogen lamp 3-1, a collimating lens 3-2, an AOTF 3-3, a focusing lens 3-4, an optical fiber combiner 3-5, a polarization maintaining fiber 3-6, a radio frequency power amplifier 3-7 and a radio frequency generator 3-8, as shown in FIG. 1. The main controller module 1 controls the radio frequency generator 3-8 to generate a signal with a specified frequency. The signal is amplified by the radio frequency power amplifier 3-7 and the amplified signal is output to the AOTF 3-3. The main controller module control the halogen lamp 3-1 to turn on and emits the polychromatic light beam. The polychromatic light beam is collimated by the collimating lens 3-2, and then is incident to the AOTF 3-3. The polychromatic light beam passes through the AOTF 3-3, to generate two beams of positive and negative first-level near-infrared monochromatic light with orthogonal polarization states. Two light beams are coupled into the polarization maintaining fiber 3-6 through the focusing fiber lens 3-4. The light beams pass through the optical fiber combiner 3-5, to generate a beam of near-infrared orthogonal polarization monochromatic light. The near-infrared orthogonal polarization monochromatic light is transmitted to the detection probe module 4 by the polarization maintaining fiber 3-6.

Figure 2:
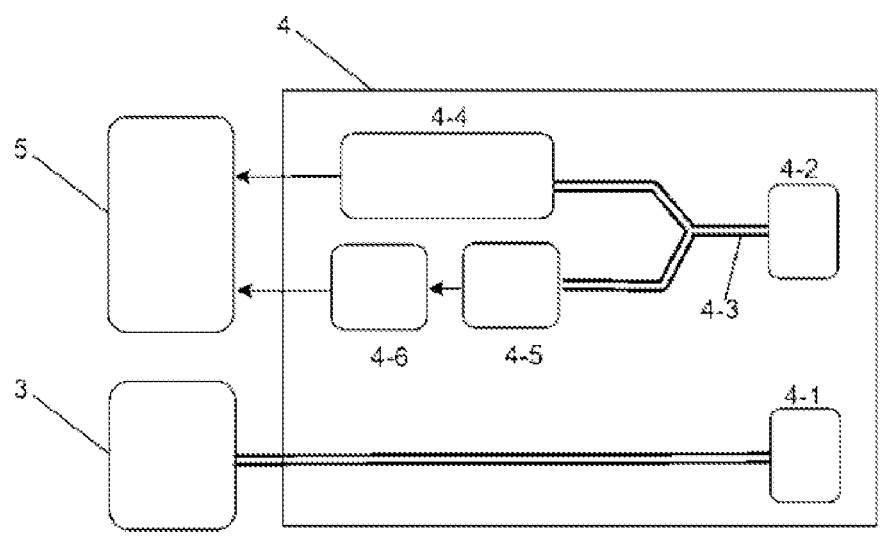
FIG. 2 is a composition diagram of the probe module.

The detection probe module 4 includes a transmitting probe unit 4-1, a receiving probe unit 4-2, a Y-shaped polarization maintaining fiber 4-3, a near-infrared photoelectric detector 4-4, an analyzer 4-5 and a photoelectric receiver 4-6, as shown in FIG. 2. The AOTF monochromatic light source module 3 transmits near-infrared orthogonal polarization monochromatic light to the transmitting probe unit 4-1 through the polarization maintaining fiber. The light beam reflected by the detection part is received by the receiving probe unit 4-2. The receiving probe unit 4-2 couples the received light beam to output into the Y-shaped polarization maintaining fiber 4-3. The light beam splits into two beams by the Y-shaped polarization maintaining fiber 4-3. One beam enters the near-infrared photoelectric detector 4-4 to generate a near-infrared intensity signal; and the other beam enters the aforementioned analyzer 4-5, and then is received by the photoelectric receiver 4-6. The photoelectric receiver 4-6 generates a light intensity signal with deflection angle information. The near-infrared light intensity signal and polarization angle signal are transmitted to the data processing module 4 for processing. The data processing module 4 amplifies and filters the near-infrared photoelectric intensity signal and the polarization angle signal, and performs an analog-to-digital conversion on the processed near-infrared photoelectric intensity signal and the polarization angle signal, and transmits to the main controller module 1 the signal on which the analog-to-digital conversion is performed. The main controller module 1 analyzes the signal and predicts the blood glucose value.

The disclosure also provides a non-invasive blood glucose measurement method which is a combination of near-infrared spectroscopy non-invasive blood glucose detection technology and non-invasive blood glucose detection technology based on optical polarimetry. The method includes the following steps.

Step 1: changing a wavelength of the near-infrared orthogonal dual-polarization monochromatic light output by the AOTF monochromatic light source 3 with 5 nm as a step from the wavelength of 900-2000 nm, collecting near-infrared intensity data and polarization angle data at 220 sampling points, and storing the data of the 220 sampling points into the main controller module 1;

Step 2: predicting a final blood glucose value in a random forest algorithm and a data fusion algorithm by the main controller module, wherein in the step 2, the blood glucose concentration is predicted by following steps:

Step 2-1: performing digital filtering and correction on the stored 220 near-infrared light intensity data and 220 light beam polarization angle data by the main controller module 1;

Step 2-2: after the digital filtering and correction, obtaining a blood glucose value BG1 predicted by a near-infrared spectroscopy and a blood glucose value BG2 predicted by an optical polarimetry in a random forest algorithm respectively;

Step 2-3: performing, by the main controller module 1, correlation analysis on blood glucose values predicted by the two methods; distributing weights according to correlation analysis results; and performing data fusion according to a following formula to calculate a final blood glucose concentration:

$$BG = a*BG1 + b*BG2 + c$$

where a and b are weights obtained by the correlation analysis, c is a correction coefficient, and an obtained blood glucose value BG is controlled and displayed on the display module 2 through the main controller module 1.

The above is only preferred embodiments of the disclosure, and does not limit the scope of the present invention. Any equivalent structure or equivalent processes transformation made by using the description and drawings of the disclosure, or directly or indirectly used in other related technical fields, is similarly included in the scope of patent protection of the disclosure.

The invention claimed is:

1. A non-invasive blood glucose detection device based on a multi-technology integration, comprising a main controller module, a display module, an acousto-optic tunable filter (AOTF) monochromatic light source module, a detection probe module and a data processing module; wherein:
the main controller module controls the AOTF monochromatic light source module to generate near-infrared orthogonal polarization monochromatic light which is transmitted to the detection probe module through an optical fiber; the detection probe module emits the near-infrared orthogonal polarization monochromatic light to a detection part; the detection probe module collects the near-infrared orthogonal polarization monochromatic light reflected by the detection part and converts an optical signal into an electric signal with polarization information and absorption intensity information; the detection probe module transmits the electric signal to the data processing module; the data processing module processes the electric signal and performs an A/D conversion on the electric signal, and then transmits the converted signal to the main controller module; the main controller module predicts a blood glucose value and displays the predicted blood glucose value on the display module.

2. The non-invasive blood glucose detection device based on a multi-technology integration according to claim 1, wherein
the AOTF monochromatic light source module comprises a halogen lamp, a collimating lens, an AOTF, a focusing lens, an optical fiber combiner, a polarization maintaining fiber, a radio frequency power amplifier and a radio frequency generator; and wherein the main controller module controls the radio frequency generator to generate a signal with a specified frequency, the signal is amplified by the radio frequency power amplifier and the amplified signal is output to the AOTF; the main controller module control the halogen lamp to turn on and emits a polychromatic light beam; the polychromatic light beam is collimated by the collimating lens, and then is incident to the AOTF; the polychromatic light beam passes through the AOTF, to generate two beams of positive and negative first-level near-infrared monochromatic light with orthogonal polarization states; two light beams are coupled into the polarization maintaining fiber through the focusing fiber lens; the light beams pass through the optical fiber combiner, to generate a beam of near-infrared orthogonal polarization monochromatic light; the near-infrared orthogonal polarization monochromatic light is transmitted to the detection probe module by the polarization maintaining fiber.

3. The non-invasive blood glucose detection device based on a multi-technology integration according to claim 1, wherein
the detection probe module comprises a transmitting probe unit, a receiving probe unit, a Y-shaped polarization maintaining fiber, a near-infrared photoelectric detector, an analyzer and a photoelectric receiver; and wherein the AOTF monochromatic light source module transmits the near-infrared orthogonal polarization monochromatic light to the transmitting probe unit through the polarization maintaining fiber; the light beam reflected by the detection part is received by the receiving probe unit, the receiving probe unit couples the received light beam to output into the Y-shaped polarization maintaining fiber; the light beam splits into two beams by the Y-shaped polarization maintaining fiber, one beam enters the near-infrared photoelectric detector to generate a near-infrared intensity signal, and the other beam enters the analyzer and then is received by the photoelectric receiver; the photoelectric receiver generates a light intensity signal with deflection angle information; the near-infrared light intensity signal and the light intensity signal with deflection angle information are passed to the data processing module for processing, the data processing module amplifies and filters the near-infrared photoelectric intensity signal and the polarization angle signal, and performs an analog-to-digital conversion on the processed near-infrared photoelectric intensity signal and the polarization angle signal, and transmits to the main controller module the signal on which the analog-to-digital conversion is performed; the main controller module analyzes the signal and predicts the blood glucose value.

4. A method for non-invasive blood glucose measurement, applied to a non-invasive blood glucose detection device based on a multi-technology integration according to claim 1, wherein the method comprises:
step 1: changing a wavelength of the near-infrared orthogonal dual-polarization monochromatic light output by the AOTF monochromatic light source with t as the step, collecting near-infrared intensity data and polarization angle data at m sampling points, and storing the data of the m sampling points into the main controller module, wherein t is the wavelength in unit of nm;
step 2: predicting, by the main controller module, the final blood glucose value in a random forest algorithm and a data fusion algorithm, wherein in the step 2, the blood glucose concentration is predicted by following steps:
step 2-1: performing, by the main controller module, digital filtering and correction on the stored m near-infrared light intensity data and m light beam polarization angle data;
step 2-2: after the digital filtering and correction, obtaining a blood glucose value BG1 predicted by a near-infrared spectroscopy and a blood glucose value BG2 predicted by an optical polarimetry in a random forest algorithm respectively;
step 2-3: performing, by the main controller module, correlation analysis on blood glucose values predicted by the two methods, distributing weights according to correlation analysis results, performing data fusion according to following formula, and calculating a final blood glucose concentration:

$$BG = a*BG1 + b*BG2 + c$$

wherein a and b are weights obtained by correlation analysis, c is a correction coefficient, and an obtained blood glucose value BG is controlled and displayed on the display module through the main controller module.

5. A non-invasive blood glucose detection device based on a multi-technology integration, comprising an acousto-optic tunable filter (AOTF) monochromatic light source module and a detection probe module; wherein:
the AOTF monochromatic light source module is configured to generate near-infrared orthogonal polarization monochromatic light which is transmitted to the detection probe module through an optical fiber; the detection probe module emits the near-infrared orthogonal polarization monochromatic light to a detection part; the detection probe module collects the near-infrared orthogonal polarization monochromatic light reflected by the detection part to form an optical signal and converts the optical signal into an electric signal with polarization information and absorption intensity information; the detection probe module provides the electric signal to a circuit for prediction of a blood glucose value.

\* \* \* \* \*